United States Patent [19]

Osborn et al.

[11] 4,260,889
[45] Apr. 7, 1981

[54] DEFECT MARKER METHOD AND APPARATUS FOR USE WITH TIRE INSPECTION MACHINES

[75] Inventors: William E. Osborn, Copley; Ronald E. Symens, Canal Fulton, both of Ohio

[73] Assignee: The Firestone Tire & Rubber Company, Akron, Ohio

[21] Appl. No.: 98,148

[22] Filed: Nov. 28, 1979

[51] Int. Cl.³ .............................................. G01N 23/00
[52] U.S. Cl. ............................................... 250/358 T
[58] Field of Search ...................... 250/358 T, 358 R; 73/146

[56] References Cited

U.S. PATENT DOCUMENTS

| | | | |
|---|---|---|---|
| 2,220,246 | 11/1940 | Kizauer | 250/358 T |
| 2,272,893 | 2/1942 | Bosomworth | 250/358 T |
| 2,301,251 | 11/1942 | Capen | 250/358 T |
| 3,789,226 | 1/1974 | Green et al. | 250/358 T |
| 3,952,194 | 4/1976 | Bayonnet | 250/358 T |
| 4,088,396 | 5/1978 | Heisner et al. | 250/358 T |
| 4,207,470 | 6/1980 | Heisner et al. | 250/358 T |

*Primary Examiner*—Davis L. Willis
*Assistant Examiner*—Janice A. Howell

[57] ABSTRACT

A defect marker method and apparatus for use with tire inspection machines wherein the defect marker apparatus comprises a slide assembly, together with marker arm and marker head assemblies, with the apparatus being mounted adjacent to the inspection machine imaging unit and the marker arm and marker head assemblies being adapted to be operatively interposed between the imaging unit and the tire being inspected. The method for precisely marking a defect area on the tire being inspected includes the steps of extending the marker mechanism from an inactive position axially forward relative to the imaging unit; aligning a target so that it is perpendicular to the defect area and marking the defect area with a visually discernible mark via a stamp coaxial with the target.

24 Claims, 9 Drawing Figures

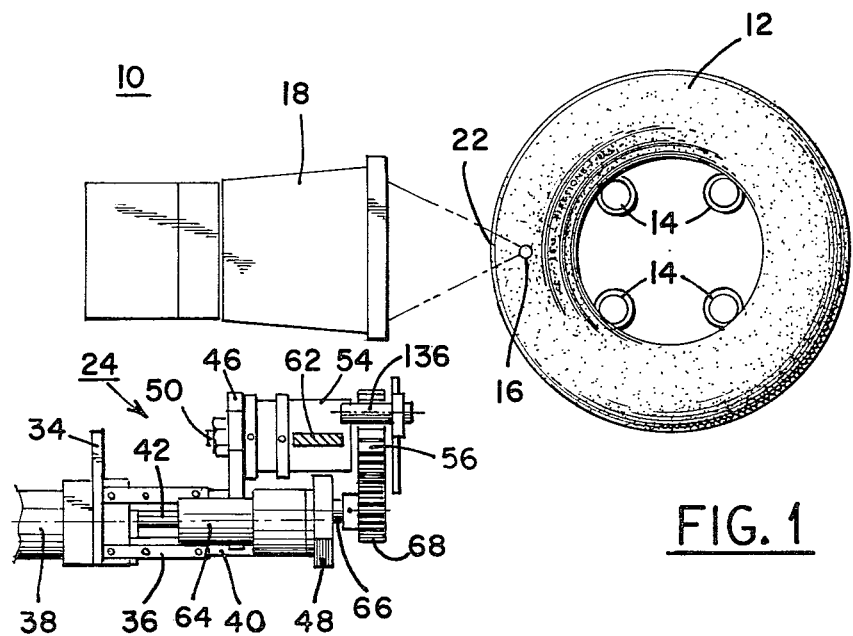
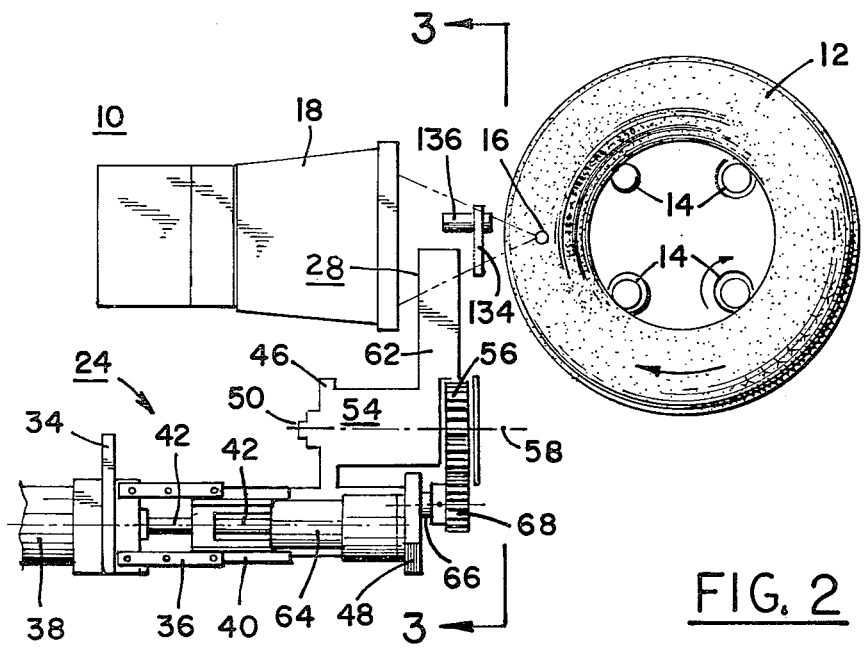

DEFECT MARKER METHOD AND APPARATUS FOR USE WITH TIRE INSPECTION MACHINES

BACKGROUND OF THE INVENTION

1. Field of the Invention

The field of art to which this invention pertains is that of tire inspection and more particularly relates to a defect marker method and apparatus for use with tire inspection machines, for example x-ray machines, used for the inspection of the internal construction of tires.

2. Description of the Prior Art

X-ray tire inspection systems are currently in use in which a tire manipulator supports a tire for rotation about its center line while an x-ray source is positioned within the torus defined by the tire. X-rays are then directed through an adjacent circumferential section of the tire in a manner well known in the art. Such system generally employ imaging units which move along orbital or arcuate paths about the exterior of the circumferential tire section to produce x-ray transparency images of the internal construction of the tire. These images are then viewed by a camera which transmits the images to a remote display screen such as a cathode ray tube monitor in an operator's booth.

This general system of inspecting tires by x-raying them has proven beneficial in locating defects not readily discernible by other means. However, it has been and continues to be difficult to pinpoint the actual location of a defect when it is observed on the remote monitor. U.S. Pat. No. 3,789,226 discloses an x-ray tire inspection machine wherein an ink spray head is located just outside of the x-ray beam. When an operator sees a defect, he actuates a reject control button that will cause an ink spray to discharge a bright colored ink on the part of the tire corresponding to the image displayed on the monitor which, however, is the part adjacent to that momentarily in the x-ray beam. Thus a segment of the tire visualized on the monitor is no longer in the axis of the imaging system but is one step removed. A related method is taught in U.S. Pat. No. 2,301,251 wherein the tire being inspected is marked at a point of defect by means of marking fluid that is projected by air under pressure. It should be noted that neither of these methods is very accurate and U.S. Pat. No. 3,789,226 even notes that the marking and subsequent diversion of the tire is to permit further inspection and repair or final rejection. In addition, spraying is environmentally detrimental to the imaging screen of the inspection machine.

U.S. Pat. No. 2,220,246 discloses a rather rudimentary inspection device wherein a defect on the tire is marked by physically actuating a marking means which places a scuff mark on the tire. Similarly, U.S. Pat. No. 2,272,893 discloses a tire inspection apparatus wherein, when a defect is found in the tire, the position may be marked via a marking means which could be chalk or crayon.

U.S. Pat. No. 3,952,194 utilizes an elastic band, having numerals thereon spaced equally around same to identify the location of a defect in a tire when the x-ray image appears on the cathode monitor so as to relate the defect discovered in the tire relative to the indicia visible on the monitor.

A further prior art method of identifying a defect includes shutting down of the x-ray machine by the operator and then physically adding a thumbtack in the approximate area of the defect and then reactivating the x-ray machine to check the location of the thumbtack relative to the defect itself.

Thus there appears to be a very definite need for precisely and accurately marking a defect in real time, i.e., while the tire is actually being viewed on the monitor. For some time, efforts have been directed toward overcoming the previously described difficulties and toward producing an improved marking device capable of rapid and accurate marking of defects within the tire construction that are not subject to the previously described disadvantages. The method and apparatus of this invention constitutes a successful culmination of such efforts.

SUMMARY OF THE INVENTION

The present invention provides a new and improved defect marker method and apparatus for use with tire inspection machines wherein tires containing an internal defect are precisely marked at the defect area while the tire is being inspected on, for example, a tire x-ray machine while the image of the portion of the tire, containing the defect, is being displayed on a remote cathode ray tube.

The defect marker apparatus includes a slide assembly attached to the imaging unit frame, with a marker arm assembly being pivotally supported on one end on the slide assembly and having a marker head assembly pivotally supported on the other end of the marker arm assembly. First actuating means is adapted to reciprocate the slide assembly from an inactive position, besides the imaging unit, to a position axially forward relative to the imaging unit, with rotary actuator means being adapted to pivot the marker arm and marker head assemblies intermediate the imaging unit and the tire being inspected. Target means and marking means, both of which form part of the marking head assembly, are adapted to be perpendicularly alignable with the tire defect area with second actuating means being utilized for replacing the target means with the marking means. Third actuating means is adapted for extending the marking means into actual physical contact with the defect area and making a visually discernible mark precisely at the defect area.

The method for precisely marking a defect area on a tire being inspected on a tire inspection machine while the image portion of the portion of the tire containing the defect is being displayed on a cathode ray tube basically includes the steps of extending the defect marker mechanism, from an inactive position besides the imaging unit, axially forward relative to the imaging unit; aligning target means on a portion of the defect marker mechanism so that the major axis of the target means is substantially perpendicular to the defect area and thereafter marking a defect area with a visually discernible mark with target means whose major axis is also coaxial with the major axis of the marking means. The aligning steps include interposing a portion of the defect marker mechanism between the imaging unit of the inspection machine and the tire being inspected while the marking step includes replacing the target means with the marker means. After the physical marking of the tire defect area, the previous steps are automatically and sequentially reversed so as to return the defect marker mechanism to its inactive position.

An important aspect of the present invention is that since the defect itself is targeted by using the imaging system of the inspection machine, the marking operation itself is free from parallax distortion and assures that each defect, no matter where it is located in the tire, is accurately and precisely marked.

Another important feature of the present invention is that when the defect marker mechanism is in its inactive or rest position it is positioned beside the imaging unit and completely removed from the actual inspection zone of the tire so that it neither obstructs the inspection zone nor is of hindrance to the operator. In operation, when an extend position is initiated by the operator, a portion of the slide assembly, carrying the marker arm and marker head assemblies, moves forward to a position axially forward relative to the imaging unit. In the pivot function, the marker arm and marker head assemblies move in an arc across the face of the imaging unit intermediate of the imaging system and the tire being inspected. By establishing the location of the defect under, for example, x-ray exposure and utilizing target means on the marker head assembly, the operator can position the target means directly over the defect area. In order to accomplish this alignment, the operator may have to use the radial and lateral movements of the inspection machine together with the pivot arc movement of the marker arm assembly. Through the use of these motions, the parallax distortion of the target is minimized and once the defect has thus been aligned relative to the target means, the operator initiates the mark function. In the mark function the marker head assembly rotates 90° and replaces the target means with marker means including a pre-inked stamp that extends out and places a visually discernible mark on the tire at the exact location of the defect. As soon as the mark has been applied, all previous movements are automatically sequentially reversed and the unit returns to its non-use position.

Other features and advantages of the invention will become more readily understood by persons skilled in the art when following the detailed description in conjunction with the several drawings.

BRIEF DESCRIPTION OF THE DRAWINGS

FIG. 1 is a fragmentary top plan view of the defect marker of the present invention in its inactive or rest position relative to the imaging system of a tire inspection machine (such as an x-ray machine) and the tire being inspected.

FIG. 2 is a view similar to that of FIG. 1 with a defect marker in its active or in-use position.

DESCRIPTION OF THE PREFERRED EMBODIMENT

Figure 5:
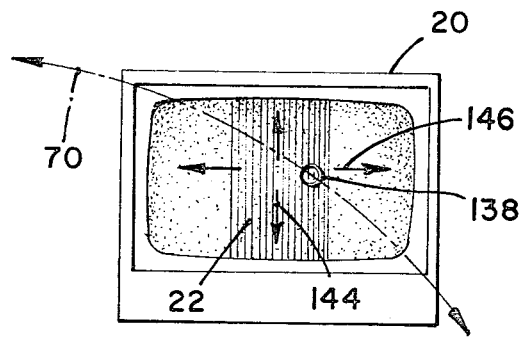
FIG. 5 is a front view of a remote video display screen on which an operator views the portion of the tire area being inspected.

Referring now to the drawings, specifically FIG. 1, there is illustrated a fragmentary top plan view of a portion of a tire inspection machine 10 which may take the form of a type 10-27-750 tire x-ray machine marketed by the Monsanto Company of St. Louis, Miss. A machine of this type is also set forth in generous detail in U.S. Pat. No. 4,088,396 to Heisner, et al. (assigned to the Monsanto Company) and for further details as to the construction and operation thereof the reader should consult this patent. It is with this type of an inspection machine that the present invention finds utility.

A tire 12 to be inspected is rotatably supported by a plurality of power driven spindles 14 that are adapted to engage the inside diameter or bead area of tire 12. Located generally within the torus of tire 12 is an x-ray tube or source 16. The x-ray picture of the portion of the tire being inspected is received by imaging unit 18 from which it is transferred in a well known manner to a cathode ray tube monitor 20 (FIG. 5) located in a remote operator's booth (not shown). As set forth in previously noted U.S. Pat. No. 4,008,396 and as also shown in U.S. Pat. No. 3,789,226 to Green, et al., the entire imaging system which includes x-ray tube 16 and imaging unit 18, is supported by a carriage moving on a pair of semi-circular parallel and vertically directed tracks so that it can be pivoted upwardly and downwardly with respect to tire 12 and can inspect the tire from one bead radially around to the other bead in a manner well known in the art. Usually the imaging system is set to inspect one zone of a tire, such as for example one sidewall, and then the tire itself is rotated 360° so that the entire annular sidewall area can be inspected.

The defect marker of the present invention, denominated by numeral 24, is mounted adjacent to imaging unit 18 and while not being operatively connected to the imaging unit, defect marker 14 is mechanically mounted to the imaging system frame and therefore moves with the imaging system in the manner previously noted.

Figure 6:
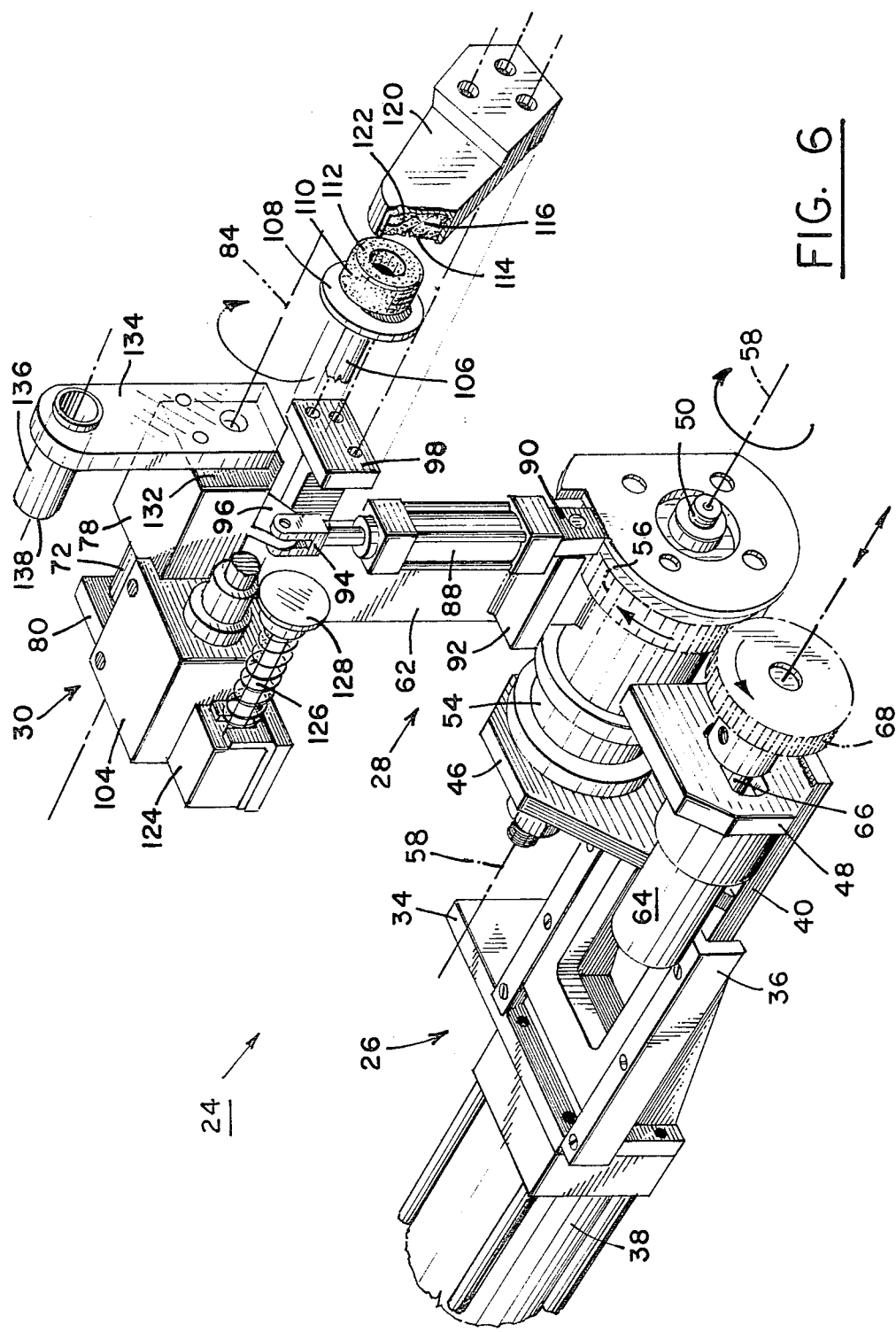
FIG. 6 is a perspective three-quarter front view, looking from the top, with some parts in exploded position for the sake of clarity, of the defect marker in its inactive position.

Turning now to FIG. 6, it shows defect marker 24 in a perspective three-quarter front view looking from the top. Defect marker 24 is made up of three main interacting elements, namely, slide assembly 26, marker arm assembly 28 and marker head assembly 30, all of which will now be described in detail.

Slide assembly 26 includes a frame bracket 34 that is fixedly attached to the imaging system frame (not shown) in any desired manner. A portion of frame bracket 34 is in turn interposed between fixed slide base member 36 and slide or first actuating means 38 which preferably takes the form of a bi-directionally or dual acting fluid pressure operated piston and cylinder apparatus. Cooperating with final slide base member 36 is moveable saddle or main frame 40, with main frame 40 being operatively connected, in any desired manner, with reciprocable piston rod 42 (FIGS. 1 and 2) of slide actuating means 38. Therefore, main frame 40 is transversely moveable relative to base member 36 and this should be clear from a perusal of FIGS. 1 and 2 wherein the former shows defect marker 24 in its inactive or rest position relative to imaging unit 18 whereas FIG. 2 shows defect marker 24 in its active or work position relative to imaging unit 18.

Fixedly attached mensially of main frame 40 is apertured vertical arm mounting bracket or holder plate 46 and vertically attached to the distal end of main frame 40 is slotted actuator bracket 48.

Rigidly affixed to apertured holder plate 46 is one end of a marker arm pivot shaft 50, with an annular quill shaft 54 being rotatably journaled thereon relative thereto. Attached to the annular end face of quill shaft 54, remote from holder plate 46, is a sector gear 56 whose axis of rotation is coincident with the axis of rotation of quill shaft 54 which in turn is coaxial with the major axis of pivot shaft 50, with all of these coincident axes being represented by axis line 58 in FIGS. 2 and 6. Also affixed to the peripheral surface of quill shaft 54 and extending radially outwardly therefrom is one end of marker arm 62 of marker arm assembly 28.

Figure 3:
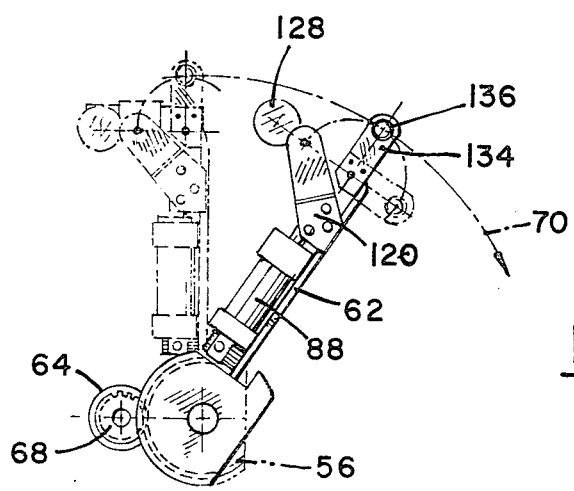
FIG. 3 is a front view of the defect marker looking the direction of arrows 3—3 in FIG. 2.

Returning now to slide assembly 26, affixed to the side of actuator bracket 48, facing frame bracket 34, is rotary actuator means 64 which preferably takes the form of an electric DC motor. Affixed to actuator means output shaft 66, which extends through an aperture in bracket 48, is drive gear 68 that is in constant mesh with sector gear 56. The energization of actuator means 64 causes marker arm assembly 28 to pivot in an arc 70 (FIGS. 3 and 5) from a rest position, where marker arm assembly 28 is adjacent to imaging unit 18, to a work position wherein marker arm assembly (and consequently marker head assembly 30) is physically interposed between imaging unit 18 and the tire being inspected, as best shown in FIG. 2.

Figure 7:
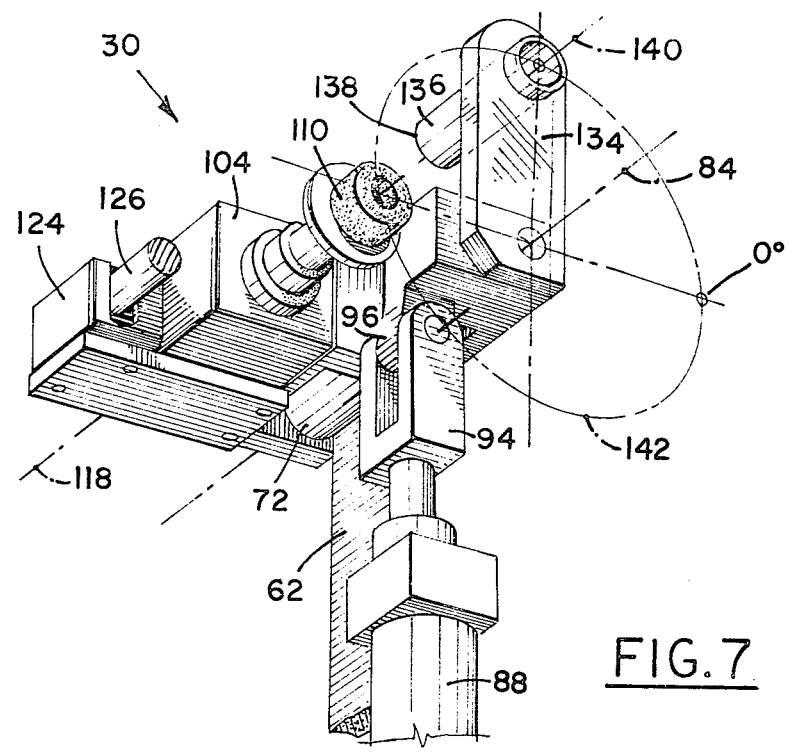
FIG. 7 is a fragmentary perspective three-quarter front view, looking from the bottom, of the marker head assembly of the defect marker, with some parts removed for the sake of clarity, in its inactive position.
Figure 8:
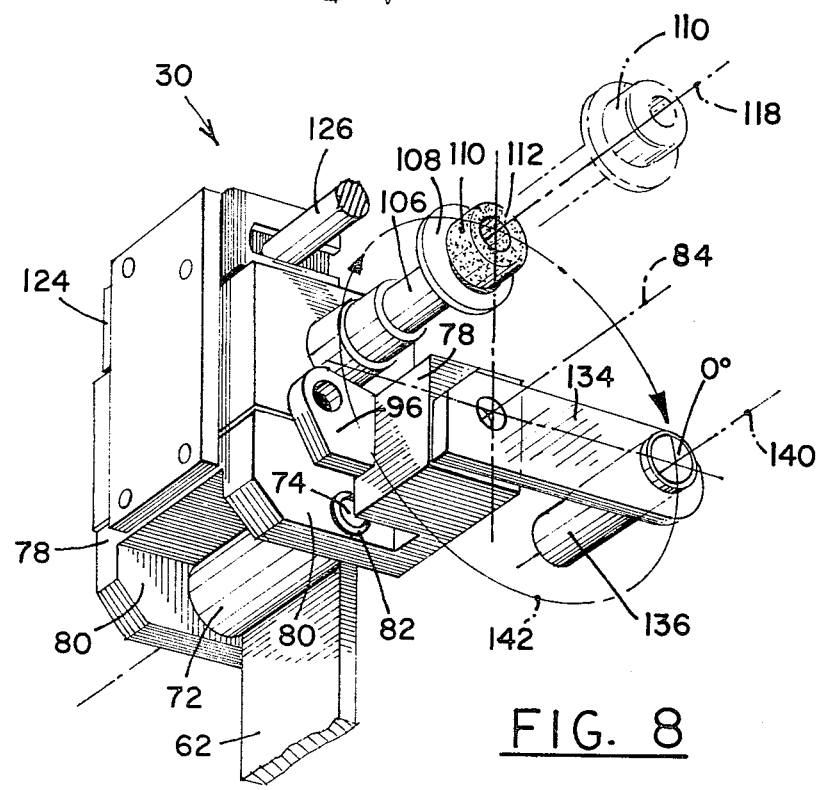
FIG. 8 is a fragmentary perspective view similar to that of FIG. 7 with the marker head assembly in its active position.

Turning now specifically to marker arm assembly 28, FIGS. 7 and 8 show that the distal end of marker arm 62 is provided with an apertured cylindrical journal member 72 having a pin 74 (FIG. 8) extending therethrough. As best seen in FIG. 8, journal member 72 is also interposed between a pair of spaced and apertured flange portions 80 of base plate 78 of marker head assembly 30. The ends of pin 74 are rotatably journaled in bushings 82 (only one of which is shown) anchored in the base plate flange portions 80. The major axis of pin 74 coincides with axis line 84 in FIGS. 6, 7 and 8, with line 84 representing the horizontal axis about which marker head assembly 30 is pivotable or rotatable relative to marker arm 62. This rotating or pivoting function is accomplished by means of a marker head or second actuating means 88 (best seen in FIG. 6) which preferably takes the form of a dual acting fluid pressure operated piston and cylinder apparatus having a clevice cap 90 on one end thereof pivotally attached to one end of a mounting pad 92 projecting from marker arm 62 close to its proximal end. A piston rod and clevice assembly 94, forming the other end portion of second actuating means 88, is pinned to an apertured boss portion or tab 96 depending from marker head base plate 78.

Turning now specifically to the structure of marker head assembly 30, attached to marker head base plate 78 is actuating means 104 which preferably takes the form of a multiple telescoping member or tube assembly that is normally biased to its inactive or collapsed position, preferably via a plurality of internal springs (not shown) and biased to its extended or operative position preferably via fluid pressure. The distal end of the smallest diameter tube or member 106 of actuating means 104 is provided with an annular flange member 108 and an outwardly extending marking means 110 which preferably takes the form of a cylindrical or annular elastic stamp having a circular or annular end face 112. The coincident major axis of both actuating means 104 and marking means 110 is denominated by line 118.

In the inactive position of marker head assembly 30, at least marker means end face 112 is kept in contact with a marking medium 114 (FIG. 6), preferably a color ink contained in a porous material 116. Material 116, preferably a felt-type material is received within a recess or opening 122 in a holder 120 which in turn is attached to an upper mounting pad 98 on marker arm 62.

Also affixed to marker head base plate 78 is a biasing means 124 (best seen in FIG. 6) which preferably takes the form of an electric solenoid whose reciprocable rod 126, having a disc 128 attached to the distal end thereof, is normally spring biased to an extended position and retractable upon an electric actuation of the solenoid core. In its normal extended position, disc 128 contacts a small sector portion of the inner side surface of annular flange 108 thus biasing marking means 110 into physical contact with porous material 116 and consequently marking medium 114 so that transfer of the latter to marker end face 112 takes place. Actuation of biasing means 124 causes the retraction of rod 126, with the disengagement of disc 128 relative to annular flange 108 permitting a slight retraction of telescoping member 106 thereby completely extracting marking means 110 from holder recess 122.

Figure 4A:
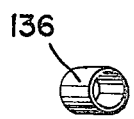
FIGS. 4a and 4b are end views of the target of the defect marker, as viewed on a remote video display screen by an operator, in the misaligned and aligned positions respectively, relative to the tire being inspected.
Figure 4B:
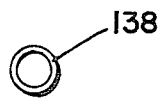

Attached to the outer or distal end face 132 of marker head base plate 78 is one end of preferably substantially transparent (both to human eyes and x-rays) plate or retainer member 134 whose apertured distal end is adapted to physically receive and retain one end of a short target means 136 which preferably takes the form of a short metallic tube that is perpendicular to plate member 134 and parallel with tubular member 106. The annular end face 138 of target means 136 (best shown in FIG. 4b) is parallel with marking means annular end face 112.

Major axis 140 of target means 136 is parallel both with pin axis 84 and major axis 118 of actuating means 104. As best seen in FIGS. 7 and 8, axes 118 and 140 are equally spaced from axis 84 and a plane passing through axes 84 and 140 is perpendicular to a plane passing through axes 84 and 118. Another way of defining this relationship is to note that axes 118 and 140 lie in a circle 142 whose center is axis 84. A perusal of FIGS. 7 and 8 will show that in the former, axes 140 and 118 pass through the 90° and 180° positions of circle 142 respectively. FIG. 8 is basically a repetition of FIG. 7 but shows marker head assembly 30 being rotated clockwise 90° so that axes 140 and 118 now occupy the zero and 90° positions in circle 142, i.e., axis 118 in FIG. 8 is now coincident with axis 140 in FIG. 7.

In operation, as tire 12 is being inspected by an operator, defect marker 24 is located adjacent to imaging unit 18 in x-ray machine 10 whereas the operator's control unit and the defect marker function control unit (neither of which control units is shown) are located in a separate operator's enclosure (not shown). The operator's control unit remotes the controls needed to operate the defect marker and the function control unit contains the logic to perform the marking function and integrates it to the x-ray computer which in turn controls the x-ray operation.

Defect marker 24 has three basic movements or functions (1) extend, (2) pivot and (3) mark. In its inactive or rest position defect marker 24 is positioned beside imaging unit 18 in the matter shown in FIG. 1. When an extend sequence is initiated by the operator, first actuating means 38 causes main frame 40, which supports marker arm assembly 28 and marker head assembly 30 to move forward (or laterally in FIG. 2) to a position wherein marker arm assembly 28 and consequently marker head assembly 30 are axially or transversely forwardly displaced relative to imaging unit 18. In the pivot function, the operator controlably energizes rotary actuator means 64 thereby causing marker arm assembly 28 (and consequently marker head assembly 30) to move in arc 70 (FIGS. 3 and 5) to move across the face of imaging unit 18 thus interposing assemblies 28 and 30 between imaging unit 18 and tire 12 being x-rayed.

It should be noted that although tire 12 is shown in FIGS. 1 and 2 as being x-rayed in the horizontal position, the operator observes the tire portion 22 being x-rayed as if it were in the vertical position with the x-ray picture of the portion of the tire rotating vertically on tube monitor 20 in FIG. 5. Thus the tire rotation can be represented by axis 144 which can also be designated the "X" axis. Similarly, the movement of the imaging system via its carriage on the C-frame tracks, can be represented by axis 146 which can also be defined as the "Y" axis. The movement of marker arm assembly 28 in arc 70 across and in front of the face of imaging system 18 can also be designated as the "Z" axis. By establishing a location of a defect in the tire under x-ray exposure and by utilizing target means 136 on marker head assembly 30, the operator can position target means 136 directly perpendicular to the defect area. To accomplish proper positioning, the operator may have to make use of the movement of one or more of the imaging system (Y axis) and of the tire (X axis) together with pivot arc 70 (Z axis) of marker arm assembly 28 to assist in the positioning. Through these multi-axis motions, the parallax distortion of the target means 136 is minimized. As noted, manipulation of one or more of the several axis permits the operator to so position target means 136 that only the target annular end face 138 (FIG. 4b) is visible on tube monitor 20. If the operator sees a portion of the sidewall of target 136 in the manner shown in FIG. 4a, i.e., when target means 136 is not perpendicular to the defect, then the target is improperly aligned. The use of transparent plate member 134 in effect suspends or presents a floating target to the operator's eyes during the alignment phase.

Once the defect has been positioned within or aligned with the target, i.e., when the target axis 140 is perpendicular to the defect, the operator initiates the mark function or sequence. This function includes two steps, namely, initially marker head assembly 30 is rotated 90° so that target means 136 is now replaced with actuating means 104. Marking means axis 118 is now perpendicular with the defect in the manner previously discussed with reference to FIGS. 7 and 8. Thereupon, actuating means 104 causes the outward movement of marking means 110 which results in the placing of a mark on tire 12 at the precise location of the defect. Actual physical contact of marking means 112 with the defect area is preferred over spraying since the latter produces sprays and vapors environmentally detrimental to the inspection machine monitor screen.

As soon as the mark has been applied, all functions are automatically sequentially reversed without any further operator input and defect marker 24 returns to its rest or non-use position, beside imaging unit 18, as shown in FIG. 1.

From the foregoing, it is believed that those familiar with the art will readily recognize and appreciate the novel concepts and features of the present invention. Obviously, while the invention has been described in relation to only one embodiment, numerous variations, changes, substitutions and equivalents will present themselves to persons skilled in the art and may be made without necessarily departing from the scope and principles of this invention. For example, the use of the defect marker is not limited for use with x-ray machines but can also be utilized with holographic inspection machines used to detect voids or air pockets, for example. As a result, the embodiment described herein is subject to various modifications, changes and the like, without departing from the scope and spirit of the invention, with the scope thereof being determined solely by reference to the claims appended hereto.

What is claimed is:

1. A method for precisely marking a defect area on a tire being inspected on a tire inspection machine while the image of the portion of said tire, containing said defect, is being displayed on a monitor screen, said method comprising the steps of: (a) extending a defect marker mechanism, from an inactive position beside the imaging unit of said inspection machine, axially forwardly relative to said imaging unit; (b) interposing a portion of said marker mechanism between said tire and said imaging system in a manner so that said portion of said mechanism is visible on said monitor screen; (c) aligning target means, on said portion of said mechanism, so that the major axis of said target means is perpendicular to said defect area; and (d) marking said defect area with a visually discernible mark via marking means whose major axis is coaxial with the major axis of said target means.

2. A method for marking according to claim 1 wherein said interposing step includes pivoting said portion of said defect marker mechanism between said imaging unit and the tire being inspected.

3. A method for marking according to claim 1 wherein said marking step includes replacing said target means with said marker means.

4. A method for marking according to claim 1 or 3 wherein said marking step includes axially outwardly extending said marking means so as to physically touch and mark said tire defect area.

5. A method for marking according to claim 4 wherein said aligning step includes movement of at least one of a portion of said inspection machine and said tire in order to minimize the parallax distortion of said target means relative to said tire defect area.

6. A method for accurately marking a defect-containing area, in the internal construction, of a tire being inspected on a tire inspection machine while the image of the portion of the tire, containing said defect area, is being displayed on a monitor screen, said method comprising the steps of: (a) extending a defect marker mechanism, from an inactive position adjacent the imaging unit of said inspection machine, axially forwardly relative to said imaging unit; (b) pivoting a portion of said defect marker mechanism, including target means, between said imaging unit and the tire being inspected in a manner so that said target means is visible on said monitor screen; (c) aligning said target means and said tire relative to one another so that said target means is perpendicular to said defect area; (d) indexing said target means so as to replace said target means with an axially aligned marking means; and (e) accurately marking said defect area by bringing said marking means into actual physical contact with and making a visually discernible mark on said defect-containing area.

7. A method for marking according to claim 6 wherein said aligning step includes movement of a portion of said inspection machine in order to minimize the parallax distortion of said target means relative to said tire defect area.

8. A method for marking according to claim 6 wherein said indexing of said target means includes rotating said target means 90° and replacing same with said marker means.

9. A method for selectively marking a defect area, in the internal construction, of a tire being inspected on a tire x-ray machine while the image of the portion of the tire, containing said defect, is being displayed on a remote cathode ray tube, said method comprising the steps of: (a) extending a defect marker mechanism, from an inactive position adjacent to the imaging unit of said x-ray machine, axially forwardly relative to said imaging unit; (b) indexing a portion of said defect marker mechanism, including target means thereon, between said imaging system and the tire being inspected in a manner so at least said target means is visible on said cathode ray tube; (c) aligning said target means, said tire and at least a portion of said x-ray machine relative to one another so that the major axis of that target means becomes perpendicular to said defect area; pivoting said target means and replacing same with marking means whose major axis is coincident with said target means major axis; and (d) selectively marking said defect area by making a visually discernible mark on said defect area.

10. A method of marking according to claim 9 wherein said marking steps includes axially outwardly extending said marking means and physically touching and marking said tire defect area.

11. A defect marker mechanism for use with a tire inspection machine for precisely marking a defect-containing area in the internal construction of a tire being inspected on said tire inspection machine while the image of the portion of said tire including said defect-containing area is being displayed on a monitor screen, said marker mechanism comprising: (a) a slide assembly having one portion thereof fixedly attached relative to the imaging unit of said inspection machine and a moveable portion adapted to be reciprocated from an inactive position, besides said imaging unit, axially forward relative to said imaging unit; (b) a marker arm pivotally supported on one end on said moveable slide portion and adapted to be pivoted intermediate said imaging unit and said tire so that at least the other end of said marker arm is visible on said monitor screen; (c) a marker head assembly, pivotally supported on said other end of said marker arm, including target means and marking means, said target means and said defect-containing area being adapted to be perpendicularly alignable relative to each other, said marker head assembly being pivotable for replacing said target means with said marking means, said marking means in turn being extendable for actual physical contact with said defect-containing area and making a visually discernible mark thereon.

12. A defect marker mechanism according to claim 11 further including first actuating means for reciprocating said moveable slide portion from an inactive position, adjacent said imaging unit, axially forwardly of but transversely displaced relative to said imaging unit.

13. A defect marker mechanism according to claim 12 further including second actuating means for pivoting said other end of said marker arm intermediate said imaging unit and said tire.

14. A defect marker mechanism according to claim 13 further including third actuating means for pivoting said marker head assembly 90° so that said target means is now replaced with the said marking means.

15. A defect marker mechanism according to claim 14 further including fourth actuating means for axially extending said marking means, said fourth actuating means taking the form of a multiple telescoping member assembly that is normally biased to its inactive position via at least one elastic member and biased as to its operative position via fluid pressure.

16. A defect marker according to claim 11 wherein said target means and said defect-containing area are perpendicularly alignable by movement at least one of said inspection machine, said tire and said marker arm, thereby permitting movement in at least one of the X, Y and Z axes.

17. A defect marker mechanism according to claim 11 or 15 further including biasing means and a marking medium, with the former normally biasing at least a portion of said marking means into contact with said marking medium prior to the actual physical contact of said marking means with said defect-containing area.

18. A defect marker mechanism according to claim 11 wherein said target means includes a retainer member, substantially transparent to both the human eye and x-rays, and a target held by said retainer means so that said target appears to float relative to the operator's eye.

19. A defect marker mechanism according to claim 18 wherein said target preferably takes the shape of a metallic tubular member whose major axis is perpendicularly alignable with said defect-containing area, with focusing relative to an annular end face of said tubular member services to minimize the parallax distortion of said target with respect to said defect-containing area.

20. A defect marker mechanism according to claim 11 wherein said marking means includes an elastic stamp.

21. A defect marker mechanism for use with a tire x-ray machine for precisely marking a defect-containing area in the internal construction of a tire being inspected on said tire x-ray machine while the image of the portion of the tire containing said defect area is being displayed on a monitor screen, said marker mechanism comprising: (a) a slide assembly having one portion thereof fixedly attached relative to the imaging unit of said x-ray machine; (b) a marker arm pivotally supported on one end of a moveable portion of said slide assembly; (c) a marker head assembly pivotally supported on the other end of said marker arm; (d) first actuating means for reciprocating said moveable portion of said slide assembly from an inactive position, beside said imaging unit, axially forward relative to said imaging unit; (e) rotary actuator means for pivoting said other end of said marker arm intermediate said imaging unit and said tire so that said marker head assembly is visible on said monitor screen; (f) target means, forming part of said marking head assembly, adapted to be perpendicularly alignable with said tire defect area; (g) marking means, forming the part of said marker head assembly, aligned with said target means; (h) second actuating means for pivoting said marker head assembly thereby replacing said target means with said marking means; and (i) third actuating means for axially extending said marking means into physical contact with said defect-containing area and making a visually discernible mark thereon.

22. A defect marker mechanism according to claim 21 wherein said target means includes a retainer member, substantially transparent to both the human eye and x-rays, and a target held by said retainer means so that said target appears to float relative to the operator's eye.

23. A defect marker mechanism according to claim 22 wherein said target preferably takes the shape of a metallic tubular member whose major axis is perpendicularly alignable with said defect-containing area, with focusing relative to an annular end face of said tubular member services to minimize the parallax distortion of said target with respect to said defect-containing area.

24. A defect marker mechanism for use with a tire x-ray machine for precisely marking a defect area in the internal construction of a tire being inspected on said tire x-ray machine while the image portion of said tire containing said defect is being displayed on a remote cathode ray tube, said marker mechanism comprising; (a) a slide assembly having one portion thereof fixedly attached relative to the imaging unit of said x-ray machine; (b) a marker arm pivotally supported on one end of another portion of said slide assembly; (c) a marker head assembly, including parallel target means and marking means adapted to be perpendicularly alignable with said defect-containing area, pivotally supported on the other end of said marker arm; (d) first actuating means operatively interconnected with said slide assembly for reciprocating said another portion of said slide assembly from an inactive position, besides said imaging unit, axially forward relative to said imaging unit; (e) rotary actuator means operatively interconnected with said slide assembly and said marker arm for pivoting said other end of said marker arm intermediate said imaging unit and said tire so that said marker head assembly is visible on said cathode ray tube; (f) second actuating means, operatively interconnected with said marker arm and said marker head assembly, for pivoting the latter and thereby replacing said target means with said marking means; and (g) third actuating means, forming part of said marking head assembly, for extending said marking means into actual physical contact with said defect-containing area and making a visually discernible mark thereon.

* * * * *